United States Patent [19]

Shirose et al.

[11] Patent Number: 4,798,601
[45] Date of Patent: Jan. 17, 1989

[54] SANITARY NAPKIN

[75] Inventors: Toshihiro Shirose; Akira Sakurai, both of Utsunomiya, Japan

[73] Assignee: Kao Corporation, Tokyo, Japan

[21] Appl. No.: 53,677

[22] Filed: May 26, 1987

[30] Foreign Application Priority Data

May 26, 1986 [JP] Japan .............................. 61-79396[U]
Jul. 25, 1986 [JP] Japan ............................ 61-114336[U]

[51] Int. Cl.[4] ............................................. A61F 13/16
[52] U.S. Cl. ..................................... 604/368; 604/378
[58] Field of Search ............... 604/358, 364, 368, 372, 604/378, 384, 385

[56] References Cited

U.S. PATENT DOCUMENTS

4,333,464  6/1982  Nakano ........................... 604/368 X
4,540,414  9/1985  Wishman .............................. 604/378
4,623,340  11/1986 Luceri ............................. 604/378 X
4,654,038  3/1987  Sakurai ........................... 604/378 X
4,666,439  5/1987  Williams et al. ..................... 604/368

Primary Examiner—Stephen C. Pellegrino
Attorney, Agent, or Firm—Birch, Stewart, Kolasch & Birch

[57] ABSTRACT

A sanitary napkin comprises a liquid-permeable surface material, a liquid-impermeable leakproof material and an absorber inserted between said surface material and said leakproof material, said absorber comprising a first absorbent paper, a second absorbent paper and an absorbent material inserted between both papers, said first absorbent paper covering at least a part of said second absorbent paper, said first absorbent paper being fixed at the portion thereof covering the second absorbent paper onto said leakproof material.

7 Claims, 4 Drawing Sheets

SANITARY NAPKIN

The present device relates to a sanitary napkin for the treatment of menstrual bleeding of women.

A purpose of the invention and device is to provide a sanitary napkin which exhibits an improvement of shape-retentivity in the production thereof without scattering the materials constituting its absorber and is excellent in absorbency.

BRIEF DESCRIPTION OF THE DRAWINGS

FIGS. 1 to 4 show examples of the napkin according to the present device, among which FIGS. 1 and 2 are transverse crosssectional views of the napkin, while FIGS. 3 and 4 are longitudinal crosssectional views thereof.

1 ... surface material
2,2' ... absorbent paper
21 ... first absorbent paper
22 ... second absorbent paper
3 ... leakproof material
4 ... cottony pulp
5 ... polymeric absorbent material
6 ... cottony staple
7 ... shift-inhibiting material
8 ... bonded area
FIG. 9 shows an example of the sanitary napkin according to the present device, wherein (a) is a plan view thereof and (b) is a crosssectional view thereof taken along line X—X'.

31 ... first absorber
32 ... second absorber
33 ... bonding between the first absorber and the second absorber
34 ... leakproof material
35 ... surface material
36,36' ... bonding between the surface material and the leakproof material
37 ... bonding between the leakproof material and the first absorber
38 ... pressure-sensitive adhesive tape
39 ... flap
40,40' ... absorbent paper
41 ... cottony pulp
42 ... highly absorbent polymer
43 ... rayon staple cotton

STATEMENT OF PRIOR ARTS

Figure 5:
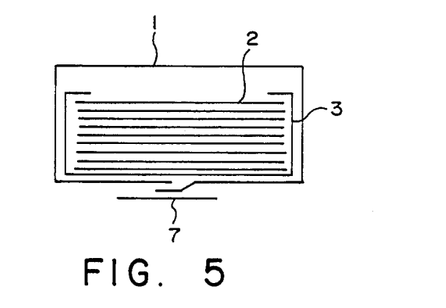
FIGS. 5 to 7 are transverse crosssectional views of the napkin according to the prior art.

An ordinary napkin comprises an absorber made of absorbent paper and/or fluff pulp, called also cottony pulp, a liquid-impermeable leakproof material covering the bottom and bottom sides of the absorber, a liquid-permeable surface material covering the whole of the absorber covered with the leakproof material and a shift-inhibiting tape attached on the non-use surface, as shown, for example, in FIG. 5 wherein numeral 1 is surface material, numeral 2 is absorbent paper, numeral 3 is leakproof material and numeral 7 is shift-inhibiting tape.

Figure 6:
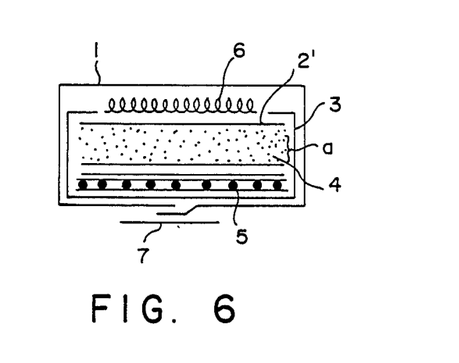
Figure 7:
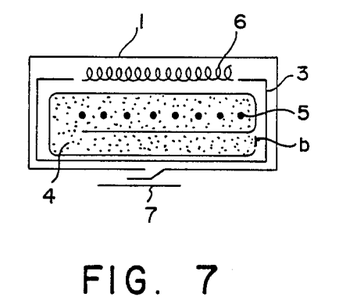

Recently, a polymeric absorbent material has been frequently used as a component constituting the absorber of a sanitary napkin for the purpose of enhancing the absorption capacity of the napkin, as shown, for example, in FIGS. 6 and 7 wherein numeral 2' is absorbent paper for piling cottony pulp, numeral 4 is cottony pulp, numeral 5 is polymeric absorbent material and numeral 6 is cottony staple.

Although a sanitary napkin containing a polymeric absorbent material as described above has been generally thought to exhibit an enhanced absorption capacity, the following problems have not been solved as yet. For example, with respect to the napkin shown in FIG. 6, a polymeric absorbent material 5 is present at a position near the non-use surface. Therefore, when the amount of menstrual blood is small, the blood is absorbed and kept by only the cottony pulp 4 or the absorbent paper 2', which is an ordinary absorbent material according to the prior art, so that the blood does not reach the polymeric absorbent material 5 to result in an ineffective use of the polymeric absorbent material 5. Further, when the cottony pulp 4 and the absorbent paper 2' are piled to produce an absorber, these constituent members each tend to shift and the cottony pulp tends to scatter from the edge thereof. The scattering cottony pulp adheres to some area of the processing line or falls down to give a product contaminated therewith which is unfavorable for sanitary reasons.

On the other hand, the napkin shown in FIG. 7 contains an absorber produced by spraying a cottony pulp 4 with a polymeric absorbent material 5 and folding the resulting pulp at the both ends into an "e"-shape. In this napkin, the shifting of the constituent members caused in the production of the absorber is remarkably reduced as compared with that of the napkin shown in FIG. 6. However, the scattering of cottony pulp still occurs from the area b, and thus the problem cannot be solved completely.

The napkin shown in FIG. 7 exhibits more excellent absorbency more than that of the one shown in FIG. 6, because the relative position of the polymeric absorbent material 5 to the use surface in the former is nearer than that in the latter. The former is superior to the latter in the effective utilization of a polymeric absorbent material. Accordingly, when the amount of menstrual blood is small, the napkin shown in FIG. 7 exhibits sufficiently excellent absorbency unlike the napkin shown in FIG. 6. However, when the amount of menstrual blood is large, the amount of the menstrual blood to be absorbed per unit volume of the absorber exceeds the absorption capacity of the absorber, because the absorber does not contain any material which can diffuse blood, for example, absorbent paper. This problem can be solved to some extent by increasing the content of a polymeric absorbent material or the amount of cottony pulp. However, these means bring about enhancement in cost and increase in thickness to lower the feeling in service, so that they are not substantially effective solutions. In other words, the napkin shown in FIG. 7 has a disadvantage in that whole thereof can be utilized.

However, the devisers of the present device think that such a napkin will still exhibit insufficient absorption characteristics, particularly side leakage, even if a highly absorbent polymer functions effectively. That is because a sanitary napkin is significantly deformed by pressure brought about by the application thereof to the crotch to cause side leakage.

Figure 11:
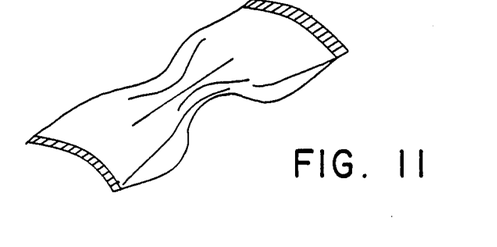
FIG. 11 is a perspective view of the form after the application to the crotch of the sanitary napkin according to the prior art.

That is to say, when a sanitary napkin is applied to the crotch, it is in a deformed (twisted) state as shown in FIG. 11, so that most of the leakage occurs from the sides in the central part of the longitudinal direction. More precisely, when pressure due to the closing of feet or walking is applied to a wet sanitary napkin containing absorbed blood therein, the napkin is twisted in the central part of the longitudinal direction, so that the distance between the both sides and the blood-absorbing area (the central part of the width direction, when the napkin is accurately worn) is reduced to cause leakage, though there are still parts wherein no blood is absorbed.

SUMMARY OF THE INVENTION

In view of the above problems, the devisers of the present device have extensively studied the construction of a sanitary napkin which is protected from deformation and twisting while in service without lowering the feeling and exhibits effectively reduced side leakage by enhancing the fitness of the napkin to the crotch and the public region and have accomplished the present device.

The present device provides a sanitary napkin comprising a liquid-permeable surface material, a liquid-impermeable leakproof material and an absorber inserted between said surface material and said leakproof material, characterized in that said absorber comprises the first absorbent paper, the second absorbent paper and an absorbent material having indeterminate form and inserted between both papers, such that the first absorbent paper wraps round at least a part of the second absorbent paper and that the first absorbent paper is bonded to said leakproof material in its area wrapping around the second absorbent paper.

A sanitary napkin of the invention, in other words, comprises a liquid-permeable surface material, a liquid-impermeable leakproof material and an absorber inserted between said surface material and said leakproof material, said absorber comprising a first absorbent paper, a second absorbent paper and an absorbent material inserted between both papers, said first absorbent paper covering at least a part of said second absorbent paper, said first absorbent paper being fixed at the portion thereof covering the second absorbent paper onto said leakproof material.

It is preferable that said absorbent material comprises fluff pulp and an absorbent polymer.

It is preferred to have a tape means to inhibit the napkin from slipping out of contact with the skin of a user.

The sanitary napkin of the invention includes such an embodiment that said absorber comprises a first absorber and a second absorber having been placed on said first absorber and having a smaller width than said first absorber, said leakproof material covers at least the bottom surface, both side surfaces and a part of the top surface of said first absorber and a part of the side surfaces of said second absorber, said surface material covers at least a part of said leakproof material and the top surface of the second absorber and fixation is made between said first absorber and said second absorber, said surface material and said leakproof material and said leakproof material and said first or second absorber.

The absorbent material having indeterminate form and inserted between the first absorbent paper and the second absorbent paper may be, for example, a laminate or a mixture of cottony pulp, called also fluff pulp, and an absorbent polymer.

The sanitary napkin according to the present device has the following advantages due to the structure described above.

(1) The entire absorber containing a polymeric absorbent material can be effectively utilized independently of whether the amount of menstrual blood to be absorbed is large or small.

(2) In the production of the napkin, the scattering of absorber-constituting materials, which causes product contamination, is inhibited so that the obtained napkin is highly hygienic.

(3) The cost is low.

(4) The shift and twist of the absorber can be inhibited.

The present device will be described in more detail by referring to the figures.

Figure 1:
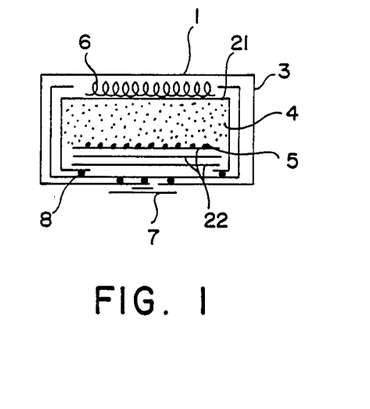
Figure 2:
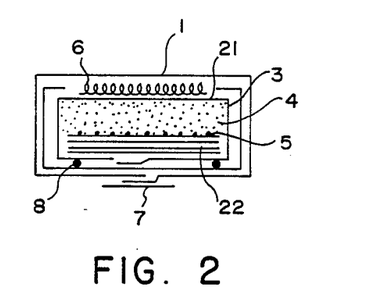
Figure 3:
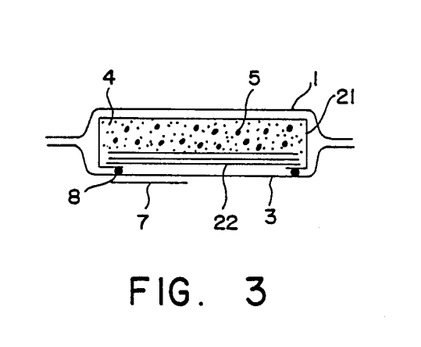
Figure 4:
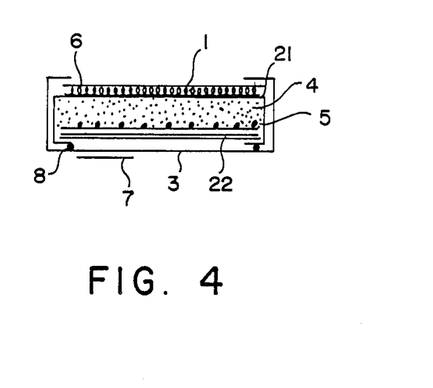

FIGS. 1 to 4 shows examples of the napkin according to the present device, among which FIGS. 1 and 2 are transverse crosssectional views (in the minor axis direction), while FIGS. 3 and 4 are longitudinal cross-sectional views (in the major axis direction). The napkin shown in FIG. 1 can be produced by piling cottony pulp 4 on the first absorbent paper 21 having a width slightly larger than that of the minor axis of the final product, spraying the piled cottony pulp 4 with a polymeric absorbent material 5 to fix the material 5 on the pulp 4, laying the second absorbent paper 22 on the sprayed pulp, folding the first absorbent paper 21 in such a way that the first absorbent paper 21 wraps round the both transverse ends of the second absorbent paper 22 to form an absorber, covering the bottom and both sides of the absorber with a leakproof material 3, bonding a part 8 of the area wrapping round the second absorbent paper 22 of the first absorbent paper 21 to the leakproof material 3, covering the whole of the obtained intermediate product with surface material 1 and fixing a shift-inhibiting tape 7 to the non-use surface.

The napkin shown in FIG. 2 is characterized by using an absorbent paper having a width larger than that of the first absorbent paper 21 used in the napkin shown in FIG. 1 as the first absorbent paper and completely wrapping round the second absorbent paper 22 in the first absorbent paper 21 in such a way that the both transverse ends of the first absorbent paper 21 overlap each other. FIGS. 3 and 4 show napkins wherein the first absorbent paper 21 wraps the both longitudinal ends of the second absorbent paper 22.

The process for bonding the area wrapping around the second absorbent paper 22 of the first absorbent paper 21 to the leakproof material 3 is not particularly limited and may be heat-bonded or adhesive-bonded.

The sanitary napkin of the present device thus produced contains a polymeric absorbent material 5 at a position near the use surface. Therefore, even when the amount of menstrual blood is small, the blood rapidly reaches the polymeric absorbent material 5 and is effectively absorbed and retained, while when the amount of blood is large, the blood is diffused in the longitudinal direction of the napkin by the second absorbent paper 22 present beneath the polymeric absorbent material 5. Thus, the whole of the sanitary napkin can effectively contribute to the absorption of blood, so that the napkin provided excellent absorbency and is free from leakage or stickiness. Further, the napkin of the present device has a structure wherein the whole edge of cottony pulp 4 is wrapped in the first absorbent paper 21 and the second absorbent paper 22, so that the scattering of cottony pulp 4 is inhibited to thereby solve hygienic problems such as product contamination. Furthermore, in the sanitary napkin of the present device, the first absorbent paper is bonded to the leakproof material, so that the leakproof material is fixed to the absorber. Therefore, the shift and twist of the absorber is remarkably reduced. The sanitary napkin of the present device is also advantageous in cost, because it only requires slight enlargement of a part of the absorbent paper of the prior art, but does not necessitate any other constituent member. Furthermore, the bonding of the first absorbent paper to the leakproof layer can be carried out by heat-bonding with a heated roll or the like or adhesive-bonding with a very small amount of an adhesive.

As discussed before, the invention includes a practical embodiment in which the first absorber and the second absorber are used which will be explained below in detail.

The present device relates to a sanitary napkin comprising the first absorber, the second absorber present on the first absorber and having a width smaller than that of the first absorber, a liquid-impermeable leakproof material covering at least the bottom, both sides and a part of the top surface of the first absorber and a part of the sides of the second absorber and a liquid-permeable surface material covering at least a part of the leakproof material and the top surface of the second absorber, wherein the fixation of the first absorber to the second absorber, that of the surface material to the leakproof material and that of the leakproof material to the first or second absorber are each so tight as not to undergo separation thereof from each other.

The present device will be further described in more detail by referring to the figures.

Figure 8:
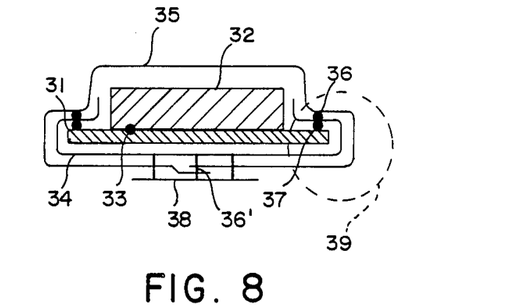
FIG. 8 is a transverse crosssectional view of a model of the sanitary napkin according to the present device.

FIG. 8 is a transverse crosssectional view of a model showing the constituent members of the sanitary napkin according to the present device. The constituent members can be arranged as follows:

(1) The absorber comprises the first absorber as lower layer and the second absorber 32 having a width smaller than that of the first absorber 31 present on the first absorber 31 nearly in the center of the first absorber.

(2) The first absorber 31 is fixed to the second absorber 32 by some means, so that they are unified by a absorber 33 which spreads over at least a part of the interfacial boundary.

(3) The bottom, the sides and a part of the top surface of the first absorber 31 and a part of the sides of the second absorber are covered with a leakproof material 34 and at least a part of the leakproof material and the top surface of the second absorber are covered with surface material 35. Thus, a flap 39 is formed.

(4) In the flap 39, the surface material 35 is fixed to the leakproof material 34 by some means to form a bonding 36 and the leakproof material 34 is fixed to the first absorber by some means to form a bonding 37.

Both bondings may each spread over at least a part of the interfacial boundary.

(5) The sanitary napkin is provided with a shift-inhibiting material 38 on the non-use surface and a part of the material 38 reaches the leakproof material 34 through the surface material 35 to form the bonding 36 between the surface material and the leakproof material.

The constituent members will be each described below together their effect.

Examples of the material constituting the first absorber 31 and the second absorber 32 include ordinary absorbent materials such as cottony pulp, absorbent paper and highly absorbent polymer and synthetic fibers such as polyethylene, polypropylene, polyester, acrylic polymer and hot-melt fiber as typified by ES fiber. These materials can be used alone or in combination thereof and neither the construction nor the mixing method are limited.

The first absorber and the second absorber are unified by a bonding 33, so that they can not be separated from each other even by pressure brought about by the application of the napkin to the crotch, thus serving to protect the napkin from deformation and twisting.

The difference in width between the first absorber and the second absorber is preferably at least 10 mm, most preferably about 30 mm. It is generally effective that the second absorber has a width of 30 to 70 mm. However, the width varies depending upon the object of the application. For example, it is suitable that the width of the second absorber of the napkin of the ordinary type is 40 to 50 mm and the width of the absorber for the treatment of light bleeding is 30 to 45 mm, while the width of for the absorber for long application or night time use is 50 to 70 mm. It has been confirmed that the napkin exhibits excellent fitness to the crotch and less deformation even under vivid motion, when the first absorber thereof has a width of 70 to 85 mm and the second absorber thereof has a width of 40 to 55 mm.

The bonding 36 of the surface material 35 to the leakproof material 34 and the bonding 37 of the leakproof material 34 to the first absorber 31 may be formed in the flap 39 by either heat sealing or by a hot melt process. The bonding 36 is preferably present at a distance of 2 to 10 mm, most preferably 3 to 5 mm, from the end of the second absorber 32. If the bonding 36 is too close to the second absorber, the absorber will be influenced by the formation of the bonding to lower the absorbency, touch and appearance. On the contrary, if the bonding 36 is too far from the second absorber, the space between the surface material and the absorber will hinder rapid transfer of the menstrual blood from the surface material to the absorber to unfavorably cause side leakage.

It is preferred that the bonding 37 is present at a distance of at least 3 mm, preferably about 5 mm, from the end of the leakproof material. When it is present at a distance of about 5 mm from the leakproof material, the menstrual blood which has been absorbed and reached the end of the second absorber can be effectively prevented from diffusing or spreading in the transverse direction to be introduced into the end of the first absorber 31.

It is preferred that the material to be used for constituting the first absorber has an absorption capacity of at least 7 g/g (at least 7 g per gram of the material) and an absolute absorption capacity of at least 3 g (one side).

The leakproof material 34 to be used in the present device may be not only an ordinary polylaminated waterproof paper obtained by laminating polyethylene or the like on one surface of a waterproof paper, but also a laminated waterproof paper obtained by laminating a resin having a relatively low melting point of 150° C. or below on one surface of a waterproof paper or by double-laminating two resins on the both surfaces.

Further, it is preferable in the napkin according to the present device that the shift-inhibiting pressure-sensitive adhesive 38, which is present on the non-use surface and is a pressure-sensitive adheisve tape or a hot melt, type adhesive reaches the back surface of the leakproof material through the surface material. In this case, the surface material 35 is fixed to the leakproof material 34 by the bonding 36 under the back surface of the first absorber 31. The bond strength of the bonding 36' is preferably enough to stand loading of at least 30 g as a whole of the napkin.

As described above, the sanitary napkin according to the present device is characterized in that it is essentially constituted by a main absorber (second absorber) which has a small width and therefore is fit to the crotch and a flap-forming absorber (first absorber) and that the fixation of the first absorber to the second absorber, that of the surface material to the leakproof material and that of the leakproof material to the first and second absorber is so tight as not to undergo separation thereof from each other. Accordingly, deformation and twisting of the sanitary napkin according to the present device is less than those of the prior art wherein the constituent members are partially fixed to each other or not unified, so that the members must each alone resist the deformation.

Further, the construction of the sanitary napkin according to the present device also serves to make the surface material adhere to the absorber to thereby allow rapid transfer of menstrual blood to the absorber.

Thus, the sanitary napkin according to the present device exhibits excellent proofness against side leakage and is excellent in fitness without giving the feeling of a foreign substance.

The invention provides a sanitary napkin preferably with a tape means to inhibit the napkin from slipping. The tape means will be illustrated below.

The present device provides a substantially slender sanitary napkin provided with slip inhibitors on its non-use surface, characterized in that the line formed by connecting the ends of the slip inhibitors nearer the front end of the napkin is concave.

The present device will be described in more detial by referring the figures.

Figure 14A:
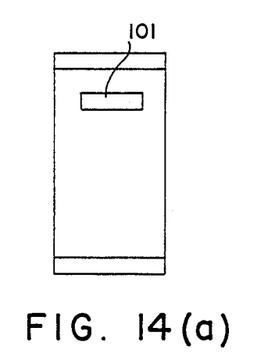
FIGS. 14 are plan views of the arrangement of slip inhibitors of the napkin according to the prior art.

FIG. 14 shows the forms of slip inhibitors provided on the non-use surface of the sanitary napkin according to the prior art, wherein FIG. 14(a) shows one of the most common forms wherein a double-coated adhesive tape 101 is transversely fixed. Most of the sanitary napkins which are now commercially available are of this type, which is called one transverse tape type. The sanitary napkin of this type is less problematic in easiness of wearing than other types, but has a disadvantage in that it is poor in a slip-inhibiting effect which is an essential object of slip inhibitors.

Figure 14B:
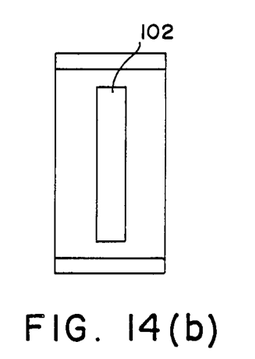

FIG. 14(b) shows the case mainly using hot-melt adhesives wherein hot-melt adhesive 102 is applied in an area longitudinally, which is called a one longitudinal tape type. Although the napkin of this type is expected to exhibit side slip inhibiting power greater than that of the napkin of the one transverse tape type, it does not really exhibit such great side power bit slip inhibiting and rather tends to frequently cause slip and uncomfortableness.

Figure 14C:
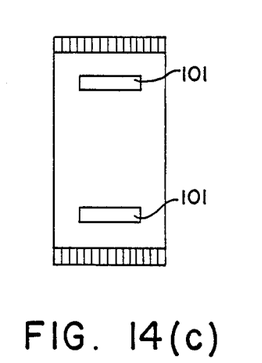
Figure 14D:
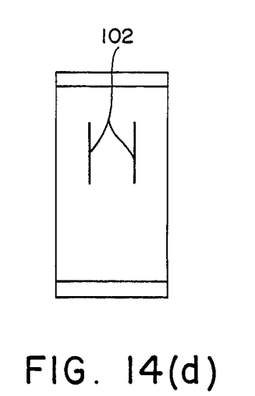

FIGS. 14(c) and (d) show the arrangement of slip inhibitors which has been proposed with the purpose of enhancing the side slip inhibiting power, among which FIG. 14(c) is a case wherein two double-coated adhesive tapes 1 are arranged transversely and FIG. 14(d) is a case wherein hot-melt adhesive 102 is applied in two areas longitudinally. The napkins of the two transverse or longitudinal tape type have a disadvantage which is substantially similar to that of the napkin of the one longitudinal tape type.

As described above, none of the slip inhibitors according to the prior art could exhibit any sufficient effect of inhibiting slip (particularly, side slip).

The sanitary napkin according to the present device is free from the disadvantages and problems of the napkins of to the prior art, so that it brings about much benefit to a user.

Figure 12:
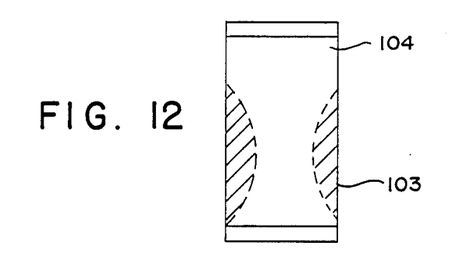
FIG. 12 is a plan view of the form of a sanitary napkin taken when the napkin is applied to the crotch or when the wearer assumes various postures 101: double-coated adhesive tape
102: hot-melt adhesive
103: area wherein significant deformation occurs in service
104: area wherein little deformation occurs in service
105: slip inhibitor
106: release paper

The devices of the present device have studied on the form of a sanitary napkin taken when a wearer assumes various postures (such as sitting or walking) and have found as a result of the studies that the hatched area 103 of the napkin shown in FIG. 12 is responds to the area which is in a bent state while the device is in service, so that the arrangement of slip inhibitors in the hatched area reduces the slip inhibiting power as described above, thus being ineffective. Accordingly, the slip inhibiting power of a slip inhibitor is thought to be effectively exhibited when the slip inhibitor is arranged in the other area 104 whereby the deformation caused by wearing and various postures is slight. Further, when no slip inhibitor is arranged in the area to be touched by a wearer in the application of the napkin to the crotch, i.e., the area near the front end, the application does not bring about adhering of adhesive to a hand, so that the napkin can be easily worn without causing uncomfortableness.

On the basis of the above finding, the devices of the present device have studied the effectiveness of slip inhibitors arranged in various forms and have confirmed that a sanitary napkin provided with slip inhibitors which are present in such a way that the line formed by connecting the ends of the slip inhibitors nearer the front end of the napkin is concave can exhibit a greater effect.

Among the sanitary napkins according to the present device, those further characterized in that the slip inhibitors are unevenly present in the front part are preferred. Particularly, among these napkins, the ones furthermore characterized in that the line formed by connecting the ends of the slip inhibitors farther apart from the front end is convex are more preferred. Further, it is preferred that the napkin is provided with at least three linear slip inhibitors.

Although the material of the slip inhibitor to be used in the present device is not particularly limited, examples thereof include double-coated adhesive tapes, pressure-sensitive adhesives and hot-melt adhesives.

According to the present device, a slip inhibitor is generally applied on the non-use surface of a sanitary napkin either by linearly discharging it from a nozzle or by linearly coating a release paper with an adhesive and transferring the adhesive to the non-use surface of a sanitary napkin, though other processes are possible. Further, the concave arrangement of the ends of slip inhibitors nearer the front end of the napkin can be easily carried out by using nozzles arranged not in a straight line but in a zigzag. The preferred width of the slip inhibitor is 3 to 6 mm.

According to the present device, there are no limits with respect to the following factors:

(1) raw materials and production process of the surface material,
(2) raw materials, amount and necessity of the cottony staple,
(3) amount of the cottony pulp,
(4) kind and content of the polymeric absorbent material,
(5) production process and amount of the absorbent paper,
(6) kind and characteristics of the polylaminated waterproof paper (kind of the laminating resin and whether the resin is applied to both surfaces or to either surface),
(7) kind, application position and amount of the shift-inhibiting material,
(8) kind, application length and amount of the adhesive,
(9) process of the heat-bonding, and the like.

The sanitary napkin according to the present device is characterized in that the absorber thereof comprises the first absorbent paper, an absorbent material having indeterminate form (for example, a laminate or a mixture comprising cottony pulp and a polymeric absorbent material) and the second absorbent paper, such that the first absorbent paper wraps round at least a part of the second absorbent paper and that the outside surface of the area wrapping round the second absorbent paper of the first absorbent paper is bonded to the inside surface of a leakproof material, so that it can be produced without scattering cottony pulp nor polymeric absorbent material and is free from the shift or twist of the absorber or the separation of the absorber from the leakproof material, all of which significantly influence the leakproofness and the absorption capacity of the sanitary napkin.

As described above in detail, the sanitary napkin according to the present device is characterized in that it is provided with slip inhibitors which are present in such a way that the line formed by connecting the ends of the slip inhibitors nearer the front end of the napkin is concave, so that no adhesive is present in the part to be touched by a wearer when wearing. Therefore, the napkin can be worn by a user without giving uncomfortableness of adhesion of the adhesive to the hand.

Further, the sanitary napkin according to the present device further characterized in that the slip inhibitors are unevenly present in the area near the front end of the napkin and that the line formed by connecting the ends of the slip inhibitors farther apart from the front end is convex is particularly advantageous in that most of the slip inhibitors are present in the front part of the napkin and less of them are present in the area which is most significantly deformed by pressure brought about when the napkin is applied to the crotch, so that the napkin can be effectively bonded to the object by the slip inhibitors and that the slip inhibitors are arranged in a form similar to that of a feather of an arrow as a whole, so that the bonding area spreads widely and effectively. Although such a wide and effective bonding area can be also attained by applying an adhesive rectangularly, this process necessitates a large amount of an adhesive as compared with the present device, resulting in enhanced cost. [

EXAMPLES]

The present device will be further described in more detail by the following Examples, though it is not limited by them.

EXAMPLES 1 TO 4 AND COMPARATIVE EXAMPLES 1 TO 3

Various napkins were produced by using the constituent members which will be described below and examined for state after wearing for 2 hours and hygienic qualities. The results are shown in Table 1.

<Constituent members>

(1) Non-woven fabric (surface material):
  Olefin non-woven fabric produced by heat-bonding
  Weight per unit area: 20 g/m$^2$
(2) First absorbent paper:
  Ordinary one made of 100% of pulp
  Weight per unit area: 18 g/m$^2$
(3) Second absorbent paper:
  Ordinary one made of 100% of pulp
  Weight per unit area: 30 g/m$^2$
(4) Leakproof material:
  A product obtained by laminating a waterproof paper having a weight per unit area of 25 g/m$^2$ and polyethylene (10μ)
(5) Cottony pulp:
  NBKP type
(6) Polymeric absorbent material:
  Polymer of acrylic derivatives (Amount; 0.3 g)

It should be understood from the results shown in Table 1 that the napkin of the present device can be produced without scattering pulp nor polymer and exhibits remarkably reduced shift and twist of the absorber and therefore provides very excellent in absorbency and feeling when worn. That is to say, the napkin is excellent of the state in service and hygienic qualities.

TABLE 1

| | Structure of napkin | State after wearing and hygienic qualities[*1] | |
|---|---|---|---|
| Comp. Ex. 1 | FIG. 5 | good | |
| Comp. Ex. 2 | FIG. 6 | The shift and twist of the absorber, the separation of the absorber from the leakproof material and the scattering of pulp were observed. | Δ |
| Comp. Ex. 3 | FIG. 7 | The shift of the absorber was not observed, but the twist of the absorber, the separation of the absorber from the leakproof material and the scattering of pulp were observed. | Δ |
| Ex. 1 | FIG. 1 | Neither the shift nor the twist of the absorber, the separation of the absorber from the leakproof material nor the scattering of pulp was observed. | |
| Ex. 2 | FIG. 2 | Neither the shift nor the twist of the absorber, the separation of the absorber from the leakproof material nor the scattering of pulp was observed. | |
| Ex. 3 | FIG. 3 | Neither the shift nor the twist of the absorber, the separation of the absorber from the leakproof material nor the scattering of pulp was observed. | |
| Ex. 4 | FIG. 4 | Neither the shift nor the twist of the absorber, the separation of the absorber from the leakproof material | |

TABLE 1-continued

| Structure of napkin | State after wearing and hygienic qualities*1 |
|---|---|
| | nor the scattering of pulp was observed. |

(Note) *1
⊙ : Neither pulp nor polymer scattered from the absorber nor from the napkin at all
∆ : Pulp and polymer slightly scattered from the absorber
▲: Pulp and polymer slightly scattered from the absorber and from the napkin

EXAMPLE 5

Figure 9A:
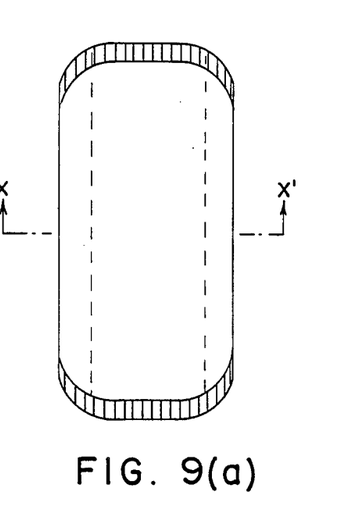
Figure 9B:
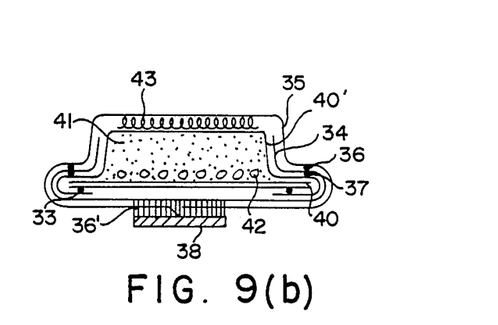

A sanitary napkin shown in FIG. 9 relates to the embodiment of the invention in which the first absorber and the second absorber are used. In the drawing, (a) is a plan view and (b) is a cross-sectional view taken along line X–X'. In the sanitary napkin shown in FIG. 9, the first absorber is made of absorbent paper 40 and the second absorber is made of cottony pulp 41 containing a highly absorbent polymer 42 and the both absorbers are covered with an absorbent paper 40', while the first absorber is fixed to the absorbent paper 40' by a bonding 33. Rayon staple cotton 43 is laid on the above absorbers and the bottom and the sides of the resulting laminate is covered with leakproof material 34 and wrapped in a surface material 35. Further, the non-use surface is provided with a pressure-sensitive adhesive tape 38. The surface material 35 is fixed to the leakproof material 34 by bonding 36', while the leakproof material 34 is fixed to the absorbent paper 40' by a bonding 37.

Figure 10:
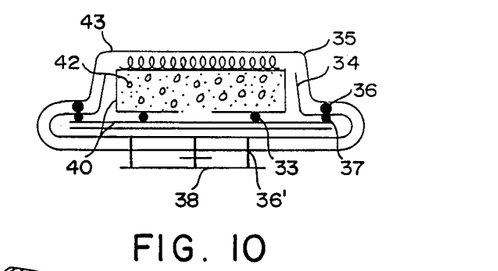
FIG. 10 is a transverse crosssectional view of another example of the sanitary napkin according to the present device.

FIG. 10 is a transverse crosssectional view of another example of the napkin according to the present device.

EXAMPLE 6

Figure 13A:
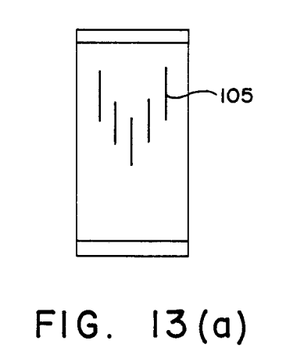
FIGS. 13 are plan views of examples of the arrangement of slip inhibitors of the sanitary napkin according to the present device.

A plurality of linear slip inhibitors 105 were applied on the non-use surface of a sanitary napkin in such a way that the line formed by connecting the ends of the slip inhibitors nearer the front end of the napkin was concave to obtain a sanitary napkin provided with slip inhibitors as shown in FIG. 13(a).

EXAMPLE 7

Figure 13B:
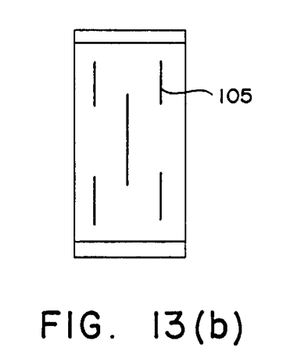

A plurality of slip inhibitors 105 were applied on a sanitary napkin in such a way that they are continuously arranged over the front part and the back part of the napkin to obtain a sanitary napkin as shown in FIG. 13(b).

EXAMPLE 8

Figure 13C:
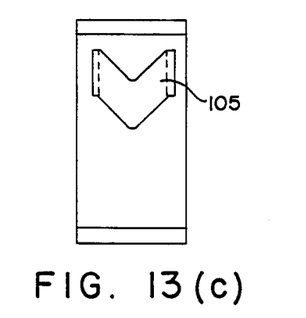

The front part of an adhesive tape used in the napkin of the above one transverse tape type was cut concavely and the back part thereof was cut convexly. The resulting cut tape was applied on a sanitary napkin to obtain a sanitary napkin as shown in FIG. 13(c).

EXAMPLE 9

Figure 13D:
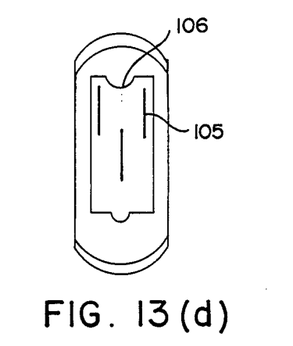

A part of the slip inhibitors was removed from a sanitary napkin as shown in FIG. 13(a). A release paper 106 was laid on the surface of the resulting napkin so as to cover the top surface of the remaining slip inhibitors with the release paper (the release paper may have any form, as far as the slip inhibitors can be completely covered with it, and particularly, easily strippable ones are preferred). Thus, a sanitary napkin as shown in FIG. 13(d) was obtained.

The obtained four napkins were examined by practical wearing. They exhibited reduced slip and twist without causing the bonding of adhesive to each other. Further, it was evaluated to be easily wearable.

What is claimed is:

1. A sanitary napkin which comprises a liquid-permeable surface material, a liquid-impermeable leakproof material and an absorber inserted between said surface material and said leakproof material, said absorber comprises a first absorber and a second absorber having been placed on said first absorber and having a smaller width than said first absorber, said leakproof material covering at least the bottom surface, both side surfaces and a portion of the top surface of said first absorber and a portion of the side surfaces of said second absorber, and said surface material covering at least a portion of said leakproof material and the top surface of the second absorber and wherein fixation is made between (a) said first absorber and said second absorber, (b) said surface material and said leakproof material and (c) said leakproof material and said first or second absorber.

2. The sanitary napkin as claimed in claim 1 in which said absorbent material comprises fluff pulp and an absorbent polymer.

3. The sanitary napkin as claimed in claim 1, which further comprises a tape means to inhibit the napkin from slipping.

4. The sanitary napkin as claimed in claim 1 wherein a portion of said bottom surface, said side surfaces and a portion of the said top surface of said first absorber and a portion of said side surfaces of said second absorber, a portion of said leakproof material and a portion of said surface material define a flap region.

5. The sanitary napkin according to claim 4 wherein said fixing of (b) and (c) occurs in said flap region.

6. The sanitary napkin according to claim 1 wherein the difference in said width of said first absorber and said second absorber is at least 10 mm.

7. The sanitary napkin according to claim 6 wherein the difference in said width of said first absorber and said second absorber is at least 30 mm.

* * * * *